United States Patent [19]

Findeisen et al.

[11] 4,434,289
[45] Feb. 28, 1984

[54] PROCESS FOR THE PREPARATION OF 2-TRIMETHYLSILYLOXY-ETHYLAMINES

[75] Inventors: Kurt Findeisen, Odenthal; Heinz Ziemann, Leichlingen, both of Fed. Rep. of Germany

[73] Assignee: Bayer Aktiengesellschaft, Leverkusen, Fed. Rep. of Germany

[21] Appl. No.: 396,515

[22] Filed: Jul. 8, 1982

[30] Foreign Application Priority Data

Jul. 24, 1981 [DE] Fed. Rep. of Germany ....... 3129272

[51] Int. Cl.³ .............................................. C07F 7/10
[52] U.S. Cl. ...................................... 546/14; 556/413; 549/505; 549/506
[58] Field of Search .......................... 556/413; 546/14; 549/505, 506

[56] References Cited

U.S. PATENT DOCUMENTS

| | | | |
|---|---|---|---|
| 2,541,154 | 2/1951 | Clapsadle | 556/413 X |
| 2,814,572 | 11/1957 | Frye | 556/413 X |
| 2,885,419 | 5/1959 | Beinfest et al. | 556/413 |
| 2,902,389 | 9/1959 | Keil | 556/413 X |

FOREIGN PATENT DOCUMENTS

| | | | |
|---|---|---|---|
| 2679 | 12/1978 | European Pat. Off. | 556/413 |
| 1157228 | 11/1963 | Fed. Rep. of Germany | 556/413 |
| 2722118 | 12/1977 | Fed. Rep. of Germany | 556/413 |

OTHER PUBLICATIONS

Methoden der Organischen Chemie (Houben-Weyl), R. Schröter, "Amine durch Reduktion", pp. 571-574.
Comptes Rendus... vol. 265, No. 9, Series C, Raymond Calas et al., pp. 516-517.
Chemical Abstracts, vol. 71, Sep. 15, 1969, No. 11, Title Page and p. 411.
Journal of Organic Chemistry, vol. 25, No. 9, Sep. 7, 1960, "The Conversion of Aldoximes . . . " Kissinger et al. and other articles, pp. 1657-1660.

*Primary Examiner*—Paul F. Shaver
*Attorney, Agent, or Firm*—Sprung Horn Kramer & Woods

[57] ABSTRACT

New 2-trimethylsilyloxy-ethylamines are disclosed. They can be prepared by catalytic hydrogenation of 1-trimethylsilyloxynitriles which are substituted in the 2-position.

16 Claims, No Drawings

PROCESS FOR THE PREPARATION OF 2-TRIMETHYLSILYLOXY-ETHYLAMINES

The invention relates to new 2-trimethylsilyloxy-ethylamines and a process for the preparation of 2-trimethylsilyloxy-ethylamines. These compounds can easily be converted into the corresponding 2-hydroxyethylamines by hydrolysis.

In many cases, reduction of cyanohydrins of aldehydes and ketones, which, as readily accessible compounds, are potential starting materials for the preparation of a large number of homologous, in some cases pharmacologically interesting, 2-hydroxyethylamines, presents considerable difficulties, both in the case of chemical reduction and in the case of catalytic hydrogenation of cyanohydrins (1-hydroxy-nitriles). The difficulties are, above all, to be attributed to the fact that the adducts of hydrogen cyanide and carbonyl compounds are in equilibrium with the starting materials, and to a particularly marked degree in the alkaline pH range, their presence leading to the formation of undesired by-products or, in the case of catalytic hydrogenation, to poisoning of the catalysts by hydrogen cyanide (Houben-Weyl, Methoden der organischen Chemie (Methods of Organic Chemistry), Volume XI/1, page 571 et seq. (1957) and Volume VI/1c, page 133 (1976)).

In the known processes for catalytic hydrogenation of 1-hydroxy-nitriles (Helv. 30, 1441 (1947), Am. Soc. 82, 4099 (1960), C.A. 67, 53293 (1967) and J. Org. Chem. 25, 1658 (1960)), platinum catalysts of palladium catalysts are used. In the known cases, large amounts of catalyst and long reaction times are required.

The parent substance of the 2-trimethylsilyloxyethylamine class of compounds, that is to say 2-trimethylsilyloxy-ethylamine, is known (Z. Obsc. Chem. 39, (1969) No. 7, pages 1462–1467). It is prepared in an expensive manner from 2 mols of ethanolamine and 1 mol of trimethylsilyl chloride. O,N-Silylated derivatives are formed as by-products.

The object of the invention is to develop a new process for the preparation of 2-trimethylsilyloxyethylamines which are substituted in the 2-position, starting from aldehydes or ketones, and hence to provide starting materials for an improved and economically acceptable preparation of 2-substituted 3-hydroxyethylamines on an industrial scale.

A process has been found for the preparation of 2-trimethylsilyloxy-ethylamines of the formula (I)

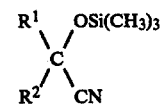

in which $R^1$ and $R^2$ are identical or different and denote hydrogen, alkyl with 1 to 18 carbon atoms, alkenyl with 2 to 12 carbon atoms, cycloalkyl or cycloalkenyl with in each case 3 to 10 carbon atoms or aryl with up to 14 carbon atoms, or together, by linking via methylene and, if appropriate, imino or oxo groups, represent a 5-membered or 6-membered ring, which is characterized in that 2-trimethylsilyloxy-nitriles, which are substituted in the 2-position, of the formula (II)

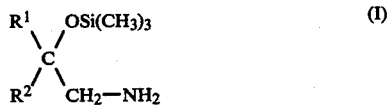

in which $R^1$ and $R^2$ have the abovementioned meaning, are reacted with hydrogen in the presence of a hydrogenation catalyst in the temperature range from 20° to 150° C. under elevated pressure.

The 1-trimethylsilyloxy-nitriles can be reacted with a low catalyst consumption and in an unexpectedly selective manner by the process according to the invention to give the 2-trimethylsilyloxy-ethylamines which are substituted in the 2-position and can easily be converted into correspondingly substituted 2-hydroxyethylamines by acid hydrolysis. Surprisingly, no complications occur in this process, as is the case in catalytic hydrogenation of cyanohydrins, even though formation of hydrogen cyanide by hydrogenolysis of the starting materials was to be reckoned with.

The process according to the invention can be illustrated with the aid of the following equation:

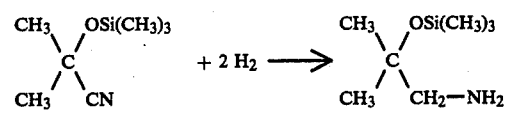

According to the invention, alkyl can be a straight-chain or branched hydrocarbon radical with 1 to 18, preferably 1 to 12, carbon atoms. A lower alkyl radical with 1 to about 6 carbon atoms is particularly preferred. The following alkyl radicals may be mentioned as examples: methyl, ethyl, propyl, isopropyl, butyl, isobutyl, pentyl, isopentyl, hexyl and isohexyl.

According to the invention, alkenyl can be a straight-chain or branched unsaturated hydrocarbon radical with 2 to 12, preferably 2 to 8, carbon atoms, and a lower alkenyl radical with 2 to about 6 carbon atoms will be particularly preferred.

The following alkenyl radicals may be mentioned as examples: vinyl, allyl, isopropenyl, butenyl, isobutenyl, pentenyl, isopentenyl, hexenyl and isohexenyl.

According to the invention, cycloalkyl can be a cyclic hydrocarbon radical with 3 to 10, preferably 5 or 6, carbon atoms. The following cycloalkyl radicals may be mentioned as examples: cyclopropyl, cyclobutyl, cyclopentyl and cyclohexyl.

According to the invention, cycloalkenyl can be an unsaturated cyclic hydrocarbon radical with 3 to 10, preferably 5 or 6, carbon atoms. The following cycloalkenyl radicals may be mentioned as examples: cyclopentenyl and cyclohexenyl.

According to the invention aryl can be an aromatic hydrocarbon with 6 to 14 carbon atoms. The following aryl-radicals may be mentioned as examples: phenyl, biphenyl and naphthyl.

It is also possible for the two radicals $R^1$ and $R^2$ to be linked together to form a 5-membered or 6-membered ring, which can optionally contain a nitrogen or oxygen atom.

Examples which may be mentioned here are the furan and pyridine rings.

The radicals according to the invention can be substituted by other radicals which do not change under the conditions according to the invention. The following radicals may be mentioned as preferred here: halogens, such as fluorine and chlorine, alkoxy, preferably lower alkoxy (1 to about 6 carbon atoms), such as methoxy, ethoxy, propoxy, isopropoxy, butoxy, isobutoxy, pentoxy, isopentoxy, hexoxy and isohexoxy, and carbalkoxy, such as carbomethoxy and carbethoxy and hydroxy.

2-Trimethylsilyloxy-nitriles of the formula (III)

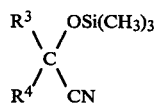
(III)

in which $R^3$ and $R^4$ are identical or different and denote hydrogen, lower alkyl, lower alkenyl cycloalkyl or cycloalkenyl with in each case 5 or 6 carbon atoms, phenyl or naphthyl or together, by linking via methylene groups and, if appropriate, an imino or oxo group, represent a 5-membered or 6-membered ring, are preferred for the process according to the invention.

The 2-trimethylsilyloxy-nitriles for the process according to the invention can be prepared by known methods (Chem. Ber. 106, 589 (1973)). They can be prepared, for example, by reacting aldehydes or ketones with trimethylsilylcyanide. Examples of aldehydes and ketones which are particularly suitable for the preparation are: formaldehyde, acetaldehyde, propionaldehyde, butyraldehyde, isobutyraldehyde, acetone, methyl ethyl ketone, isopropyl methyl ketone, cyclobutanone, cyclopropanone, cyclohexanone, 2-methylcyclohexanone, benzophenone and tetramethyl-4-piperidinone.

The process according to the invention is in general carried out in the temperature range from about 20° to 160° C. and under a hydrogen pressure of about 10 to 250 bar. It is preferably carried out in the temperature range from about 30° to 120° C., and particularly preferably in the temperature range from 25° to 80° C.

It may be advantageous to carry out the process under a higher hydrogen pressure in the range from 50 to 200 bar, and particularly preferably in the range from 80 to 120 bar.

The process according to the invention is carried out in the presence of a hydrogenation catalyst. Hydrogenation catalysts for the process according to the invention in general contain a metal of group VIII of the Periodic Table according to Mendeleeff and/or copper or at least one of these metals in combination with vanadium, chromium or manganese. Metals of group VIII of the Periodic Table which may be mentioned are: iron, cobalt, nickel, ruthenium, rhenium, palladium, osmium, iridium and platinum.

The metals mentioned can be present in the catalyst in the form of the elementary metal or in the form of a hydroxide, hydrated oxide or oxide, and can be used together with an inert support material.

Examples of inert support materials are synthetic and naturally occurring, optionally physically or chemically modified substances, such as aluminum oxides, silicic acid, kieselguhr, silicates, aluminum silicates, montmorillonites, zeolites, spinels, kaolin, clay, magnesium silicate, asbestos, pumice, dolomite, alkaline earth metal carbonates, alkaline earth metal sulphates, zinc oxide, zirconium oxide, silicon carbide, boron phosphate, aluminum phosphate, active charcoal, silk, polyamides, polystyrenes, polyurethanes and cellulose. Such supported catalysts in general contain about 1 to 65% by weight, preferably 5 to 50% by weight, of the catalytically active metal, relative to the total mass of supported catalyst. The catalytically active metals can be homogeneously distributed in the support material or, preferably, deposited in the outer layer or on the surface of the support. The preparation and shaping of the catalysts which can be used in the process according to the invention can be effected in a known manner (R. L. Augustin, "Catalytic Hydrogenation", Marcel Dekker Inc., New York (1965); and Chemical Engineering 81, 98, Book No. 20 (1974)).

Supported catalysts in the form of beads, cylinders, polygons, strands, filaments or fibres are in general preferred for carrying out the process according to the invention continuously by the fixed bed catalyst method, especially in the trickle phase, whilst unsupported catalysts or supported catalysts in pulverulent form are preferred for the discontinuous procedure in a liquid phase.

Catalysts which contain nickel are preferred for the process according to the invention. These catalysts can contain nickel by itself or in combination with at least one other of the abovementioned metals. The following are examples of preferred catalysts which may be mentioned: catalysts of the Raney type, such as Raney nickel, Raney nickel/iron, Raney nickel/cobalt and Raney nickel/copper, metallic nickel prepared by reduction of nickel salts with zinc dust, alkali metal hydrides, boranates, hydrogen boride, metal-alkyl compounds or hydrazine, such as Urushibara nickel, metallic catalysts prepared by reduction of nickel oxide or mixtures of nickel oxide and at least one other metal oxide with hydrogen, such as nickel oxide/chromium oxide, nickel oxide/manganese oxide/copper oxide and nickel oxide/chromium oxide/copper oxide, and supported catalysts, such as nickel-on-kieselguhr, nickel-on-aluminum oxide, nickel/copper-on-aluminum oxide and nickel/manganese-on-aluminum oxide.

The catalysts can contain, as an accelerator, one or more of the elements lithium, sodium, potassium, calcium, barium, silver, gold, beryllium, lanthanum, cerium, vanadium, niobium, tantalum, molybdenum and tungsten in amounts of up to 10% by weight, preferably up to 1% by weight, based on the catalytically active metal.

Particularly preferred catalysts for the process according to the invention are: Raney nickel containing more than 90% by weight of nickel and less than 1% by weight of iron, calcium and sodium; Raney nickel/iron containing 5 to 30% by weight of iron and less than 1% by weight of calcium and sodium; Raney nickel/cobalt containing 5 to 30% by weight of cobalt; Raney nickel/copper containing 5 to 20% by weight of copper; nickel/copper-on kieselguhr containing 5 to 20% by weight of copper; and nickel-on kieselguhr containing 50 to 65% by weight of nickel.

Mixtures of two or more of the catalysts mentioned can also be used for carrying out the process according to the invention. The amount of catalyst or catalyst mixture used can vary within wide limits and usually depends on the nature of the catalyst or catalyst mixture, the reaction conditions and the technological procedure. In general, the catalyst or catalyst mixture is used in an amount corresponding to 1 to 100, preferably 5 to 50, % by weight of metal, the amount being relative to the amount by weight of the 1-trimethylsilyloxy-nitriles employed. A corresponding amount of supported catalyst is, of course, used, preferably about 1.5 to 150% by weight, particularly preferably 5 to 75% by weight, relative to the amount of 1-trimethylsilyloxy-nitriles used. Since the catalysts can be reused several times, crude catalyst concentrations are also entirely economical.

The process according to the invention can be carried out in the liquid phase in the absence of a diluent. However, the reaction is preferably carried out using a diluent. Useful diluents are all the organic solvents which are inert under the reaction conditions, for example aliphatic and cycloaliphatic hydrocarbons, such as hexane, heptane, octane, cyclohexane, methylcyclohexane and decalin; aliphatic and alicyclic ethers, such as diethyl ether, dipropyl ether, diisopropyl ether, dibutyl ether, dimethylbutyl ether, methyl butyl ether, ethyl butyl ether, ethylene glycol dimethyl ether, 1,3-dioxolane, 1,4-dioxane and tetrahydrofuran; lower aliphatic alcohols, such as methanol, ethanol, propanol, isopropanol, butanol, iso-butanol, tert.-butanol and ethylene glycol; and ether-alcohols, such as diethylene glycol, ethylene glycol monomethyl ether, ethylene glycol monobutyl ether and dipropylene glycol.

One can also use mixtures of the above diluents or solvents.

Diluents or solvents which are preferred for the process according to the invention are cycloaliphatic hydrocarbons, alicyclic ethers and lower aliphatic alcohols. Cyclohexane, methylcyclohexane, methanol, ethanol, iso-propanol, tetrahydrofuran and 1,4-dioxane are particularly preferred.

The process according to the invention can be carried out discontinuously or continuously in a known manner as bottom-phase hydrogenation in known hydrogenation equipment, such as autoclaves, tube reactors, circulatory units, for example loop reactors, or cascades of autoclaves.

It may also be advantageous to carry out the hydrogenation continuously in the trickle phase or gas phase on a catalyst, preferably in the form of lumps, arranged as a fluidized bed.

In a simple embodiment, the process according to the invention can be carried out, for example, as follows:

An autoclave is filled with the starting material, the catalyst and the diluent are added and the autoclave is closed. The air is then expelled in a known manner by flushing with nitrogen and hydrogen and the autoclave is then put under the chosen hydrogen pressure. The autoclave is subsequently heated to the chosen reaction temperature, with intensive stirring of the reaction mixture.

The course of the hydrogenation can easily be followed by measuring the hydrogen consumption, which is compensated by supplying further hydrogen. The hydrogenation has ended when no further hydrogen is taken up, the amount of hydrogen taken up approximately corresponding to the theoretically required amount of hydrogen.

The reaction time required varies depending on the starting material, reaction temperature, hydrogen pressure, intensity of mixing and nature and amount of catalyst. In general, it is a half to several hours.

When the hydrogenation has ended, the reaction mixture can be worked up in a known manner, for example by filtering off the catalyst and, if appropriate, distilling off the diluent. The resulting crude hydrogenation product in general contains only small amounts of impurities and can be purified in the usual manner, for example by distillation or extraction.

By the process according to the invention, 2-trimethylsilyloxy-ethylamines can advantageously be prepared in a high yield and purity using commercially available catalysts in the reactors usually employed industrially for pressure hydrogenation, from readily accessible starting materials or industrial mixtures of these starting materials.

It is surprising that 1-trimethylsilyloxy-nitriles can be converted completely and selectively into 2-trimethylsilyloxy-ethylamines, even though complications were to be expected as a result of poisoning of the hydrogenation catalyst.

The new 2-trimethylsilyloxy-ethylamines of the formula

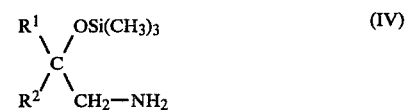

in which $R^1$ and $R^2$ are identical or different and denote hydrogen, alkyl with 1 to 18 carbon atoms, alkenyl with 2 to 12 carbon atoms, cycloalkyl or cycloalkenyl with in each case 3 to 10 carbon atoms, or aryl with up to 14 carbon atoms, or together, by linking via methylene and, if appropriate, imino or oxo groups, represent a 5-membered or 6-membered ring, $R^2$ being other than hydrogen if $R^1$ is hydrogen, can be prepared by the process according to the invention.

The 2-trimethylsilyloxy-ethylamines which are readily accessible by the process according to the invention can easily be converted, with dilute acids, into 2-hydroxyethylamines, which, according to Houben-Weyl, Volume XI/1, page 571, are pharmacologically interesting compounds.

In addition, the 2-trimethylsilyloxy-ethylamines which are now readily accessible are intermediates for the synthesis of ureas and amides with a protected hydroxyl group.

The 2-trimethylsilyloxy-ethylamines according to the invention can be used as stabilizers in a manner similar to the compounds known from German Offenlegungsschrift No. 2,642,446 and as light stabilizers in a manner similar to the compounds known from Japanese Application No. 55/018,409.

The 2-trimethylsilyloxy-ethylamines according to the invention can be used for the synthesis of sympathomimetics, e.g. OCTOPAMIN (Ernst Mutschler, "Arzneimittelwirkungen", 4. Auflage, Wissenschaftliche Verlagsgesellschaft mbH, Stuttgart 1981). The synthesis can be illustrated with the aid of the following equations:

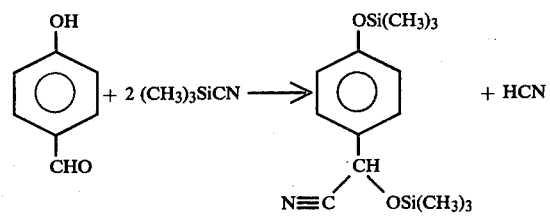

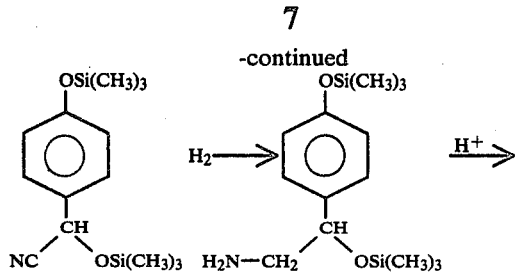

ended, the catalyst is removed, the solvent is distilled off and the residue is fractionated.

Yield: 191 g of 1-trimethylsilyloxy-1-aminomethylcyclohexane (=95% of theory);

Boiling point: 100° to 103° C. under 18 mbar.

EXAMPLES 3 to 7

The preparation is carried out in a manner corresponding to that in Example 2.

| Example | Starting material | End product | Yield (%) | Boiling point |
|---|---|---|---|---|
| 3 | NC, OSi(CH₃)₃ on 2,2,6,6-tetramethylpiperidine | H₂N—CH₂, OSi(CH₃)₃ on 2,2,6,6-tetramethylpiperidine | 92 | 131–133° C. under 16 mbar |
| 4 | (CH₃)₂C(OSi(CH₃)₃)(CN) | (CH₃)₂C(OSi(CH₃)₃)(CH₂—NH₂) | 84 | 46–48° C. under 16 mbar |
| 5 | (C₆H₅)₂C(OSi(CH₃)₃)(CN) | (C₆H₅)₂C(OSi(CH₃)₃)(CH₂—NH₂) | 81 | 130–132° C. under 0.3 mbar |
| 6 | cyclohexenyl-CH(CN)(OSi(CH₃)₃) | cyclohexenyl-CH(CH₂—NH₂)(OSi(CH₃)₃) | 87 | 122–125° C. under 19 mbar |
| 7 | CH₃—CH(CN)(OSi(CH₃)₃) | CH₃—CH(CH₂—NH₂)(OSi(CH₃)₃) | 91 | 119–122° C. |

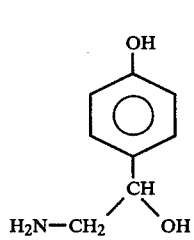

EXAMPLE 1

171 g (1 mol) of 1-trimethylsilyloxy-2-methylbutyronitrile are dissolved in 800 ml of dioxane and are hydrogenated in an autoclave together with 35 g of Raney nickel at 60° C. and under 100 bar of hydrogen for 5 hours. The hydrogen uptake has then ended. The catalyst is filtered off, the solvent is distilled off and the residue is fractionated.

Yield: 143.5 g of 2-trimethylsilyloxy-3-methyl-butylamine (=82% of theory);

Boiling point: 68° to 70° C. under 18 mbar.

EXAMPLE 2

197 g (1 mol) of 1-trimethylsilyloxy-1-cyanocyclohexane are dissolved in 600 ml of tetrahydrofuran, 40 g of Raney nickel are added and the mixture is hydrogenated in an autoclave at 60° C. and under 90 bar of hydrogen for 3 hours. When the uptake of hydrogen has

EXAMPLE 8

197 g (1 mol) of 1-trimethylsilyloxy-1-cyanocyclohexane are dissolved in 700 ml of dioxane, 40 g of Ru/Al₂O₃ are added and the mixture is hydrogenated in an autoclave at 130° C. and under 140 bar of hydrogen for three hours. When the uptake of hydrogen has ended, the catalyst is removed, the solvent is distilled off and the residue is fractionated.

Yield: 170.9 g of 1-trimethylsilyloxy-1-aminomethylcyclohexane (=85% of theory)

Boiling point: 100°–103° C. under 18 mbar.

EXAMPLE 9

197 g (1 mol) of 1-trimethylsilyloxy-1-cyanocyclohexane are dissolved in 700 ml of dioxane, 40 g of Ni chromite are added and the mixture is hydrogenated in an autoclave at 110° C. and under 90 bar of hydrogen for three hours. When the uptake of hydrogen has ended, the catalyst is removed, the solvent is distilled off and the residue is fractionated.

Yield: 164.8 g of 1-trimethylsilyloxy-1-aminomethylcyclohexane (82% of theory)

Boiling point: 100°–103° C. under 18 mbar.

What is claimed is:

1. A trimethylsilyloxy-ethylamine of the formula

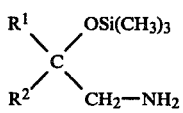

wherein $R^1$ and $R^2$ are identical or different and denote hydrogen, alkyl with 1 to 18 carbon atoms, alkenyl with 2 to 12 carbon atoms, cycloalkyl or cycloalkenyl with in each case 3 to 10 carbon atoms or aryl with up to 14 carbon atoms, or together, by linking via at least one methylene group which link can contain an amino or oxo group, represent a 5-membered or 6-membered ring, $R^2$ being other than hydrogen if $R^1$ is hydrogen.

2. A 2-trimethylsilyloxy-ethylamine according to claim 1, which is 2-trimethylsilyloxy-3-methylbutylamine.

3. A 2-trimethylsilyloxy-ethylamine according to claim 1, which is 1-trimethylsilyloxy-1-amino-ethyl-cyclohexane.

4. A 2-trimethylsilyloxy-ethylamine according to claim 1, of the formula

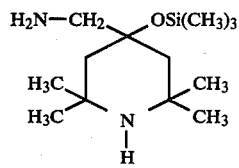

5. A 2-trimethylsilyloxy-ethylamine according to claim 1, of the formula

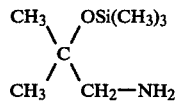

6. A 2 trimethylsiloxy-ethylamine according to claim 1 of the formula

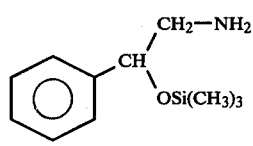

7. A 2-trimethylsiloxy-ethylamine according to claim 1, of the formula

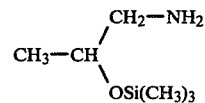

8. A process for the preparation of a 2-trimethylsiloxy-ethylamine of the formula

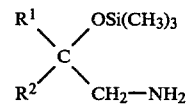

wherein $R^1$ and $R^2$ are identical or different and denote hydrogen, alkyl with 1 to 18 carbon atoms, alkenyl with 2 to 12 carbon atoms, cycloalkyl or cycloalkenyl with in each case 3 to 10 carbon atoms or aryl with up to 14 carbon atoms, or together, by linking via one or more methylene groups which link can contain an imino or oxo group, represent a 5-membered or 6-membered ring, which comprises contacting a 2-trimethylsilyloxy-nitrile, of the formula

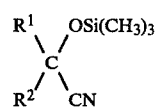

wherein $R^1$ and $R^2$ have the meaning given above with hydrogen in the presence of a hydrogenation catalyst at a temperature from 20° to 150° C. under elevated pressure.

9. A process according to claim 8, wherein said hydrogenation catalyst contains a metal from group VIII of the Periodic Table according to Mendeleeff and/or copper or at least one of the metals in combination with vanadium, chromium or manganese, in metallic and/or oxidic form.

10. A process according to claim 9, wherein said catalyst contains nickel in metallic and/or oxidic form.

11. A process according to claim 8, wherein said catalyst is employed in an amount corresponding to 1 to 100% by weight of metal, relative to the amount of 1-trimethylsilyloxy-nitrile employed.

12. A process according to claim 8, wherein the hydrogenation is effected at a temperature of 30° to 120° C.

13. A process according to claim 8, wherein the hydrogenation is carried out under a partial pressure of hydrogen of about 10 to 150 bar.

14. A process according to claim 8, wherein the process is carried out in the presence of a diluent.

15. A process according to claim 8, wherein the process is carried out in the presence of a cyclic ether diluent.

16. A process according to claim 8, wherein the process is carried out in the absence of a diluent.

* * * * *